US00PP08232P

United States Patent [19]

Jessel, Jr.

[11] Patent Number: Plant 8,232

[45] Date of Patent: May 18, 1993

[54] CARNATION PLANT NAMED CFPC DAYDREAM

[75] Inventor: Walter H. Jessel, Jr., Salinas, Calif.

[73] Assignee: California Florida Plant Co., L.P., Salinas, Calif.

[21] Appl. No.: 757,832

[22] Filed: Sep. 11, 1991

[51] Int. Cl.[5] ..... H01H 5/00

[52] U.S. Cl. ..... Plt./70.1

[58] Field of Search ..... Plt./70.1, 70.3, 73.2

*Primary Examiner*—Howard J. Locker

*Attorney, Agent, or Firm*—Christie, Parker & Hale

[57] ABSTRACT

A new carnation of white, picotee pink coloration.

1 Drawing Sheet

SUMMARY OF THE INVENTION

The present invention relates to a new and distinct variety of caarnation plant which was originated by me in a controlled breeding program by my crossing as seed parent, an unnamed and unpatented seedling of my creation and as pollen parent the variety known as 'Heidi'. The varietal denomination of this new carnation is 'CFPC Daydream'.

Among the novel combination of characteristics possessed by the new variety which distinguishes it from its parents and all other varieties of which I am aware are the attractive white, picotee pink flower coloring, which have good vase life and resistance to Botrytis. Flowers of the new variety are produced as large-size standards.

Asexual reproduction by propagation by side shoot cuttings of the new variety as performed in Fremont and Salinas, Calif., shows that the foregoing and other distinguishing characteristics come true to form and are established and transmitted through succeeding propagations. Although propagation by side shoot cuttings is described, other known methods of asexual reproduction may also be used to reproduce 'CFPC Daydream'.

BRIEF DESCRIPTION OF THE ILLUSTRATION

The accompanying illustration show a typical specimen of the flowers of the new variety in full bloom and depicted in color as nearly true as it is reasonably possible to make the same in a color illustration of this character.

DESCRIPTION OF THE NEW VARIETY

The following is a detailed description of my new variety, with color terminology in accordance with the Royal Horticultural Society Colour Chart (RHSCC). The terminology used in the color description herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Fremont and Salinas, Calif. The height of plant and flower and foliage size are established as an average using standard commercial cultural practices.

Name: CFPC Daydream.

Classification:

*Botanical.*—*Dianthus caryophyllus.*

*Commercial.*—Carnation, standard type.

Parentage:

*Female parent.*—Unnamed seedling (No. 1125).

*Male parent.*—'Heidi'.

Plant:

*Height.*—About 40 inches.

*Growing habit.*—Herbaceous, semi-upright.

*Blooming habit.*—Standard disbud type.

*Blooming season.*—Year round.

*Rooting time.*—About 13-15 days.

*Mutation prone.*—Does not appear to be.

*Disease resistance.*—Unknown.

*Temperature tolerance.*—Typical for carnation.

*Breaking action.*—Very good.

Foliage:

*Color.*—Upper side: Near to 139A. Lower side: Near to 139B.

*Size.*—About 5½ inches long, about ½-inch wide at base of plant.

*Quantity.*—Numerous.

*Shape.*—Lanceolate.

*Texture.*—Smooth.

*Ribs.*—Central, keeled.

*Arrangement.*—Bi-lateral along stem.

*Stem.*—Green.

Bud:

*Shape.*—Oval.

*Color.*—Near to 143A.

*Length.*—About 1⅓ inches.

*Diameter.*—About ½-inch.

Calyx:

*Number of sepals.*—About 6.

*Length.*—About 1⅓ inches

*Width.*—About ½-inch.

*Color.*—Outside — near to 143A. Inside — near to 145C.

Bloom:

*Shape.*—Round.

*Size.*—Diameter average: About 3½ to 4-inches. Depth average: About 2-inches.

*Borne.*—Terminal as a standard.

*Color.*—General tonality: White with slight pink edge. Upper side: Whiter than 155D. Lower side: Whiter than 155D. Center: White picotee pink. Outer petals: White picotee pink (Pink color changes seasonally from near 57A to near 62C when hot, i.e. color fades).

*Keeping quality.*—2½ to 3 weeks.

*Fragranace.*—Slight.

Petals:

*Number.*—About 58 to 60.

*Outer petals.*—Length: About 2 to 2¼ inches. Width: About 1 inch.

*Central petals.*—Length: About 1⅓ inch. Width: About ¾ inch.

*Texture.*—Smooth.

*Form.*—Fan shaped.

*Appearance.*—Shiny.

Reproductive organs: Not visible in this variety.

*Stamens.*—Number: About 6 to 7. Arrangement: Around the ovary.

*Anthers.*—Number: About 6 to 7. Length: About ⅛-inch. Color: Near to 160B.

*Filaments.*—Length: About 1⅓ inches. Color: Near to 158B.

*Pistil.*—Number: About 2. Color: Style — near to from 158C to white. Length: About 2¼ inches at maturity.

*Stigma.*—Number: About 2. Color: White.

*Ovary.*—Shape: Conical, ribbed. Color: Base — greenish white. Body — greenish yellow. Apex — tan.

I claim:

1. A new and distinct variety of carnation plant, substantially as shown and described.

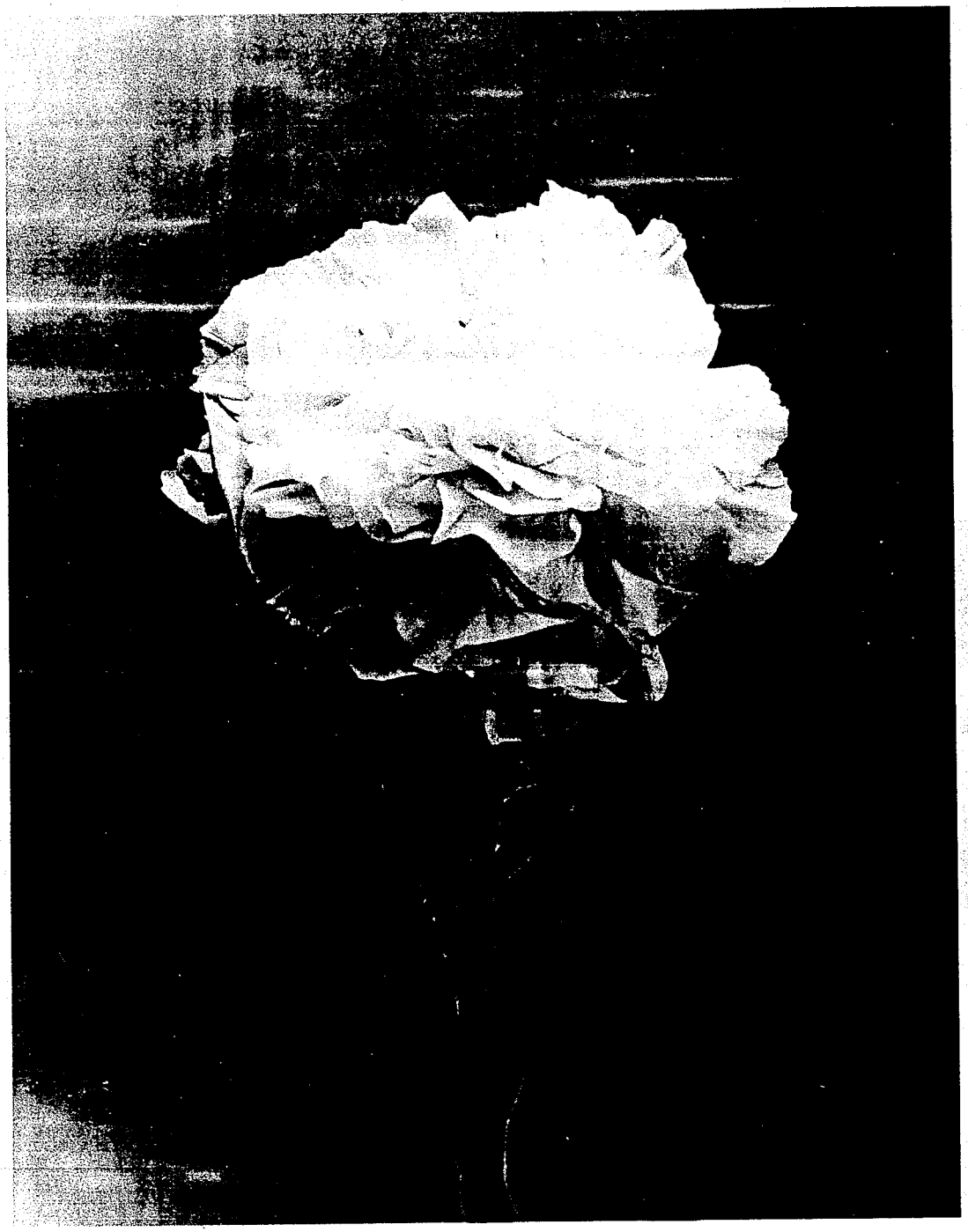

* * * * *